(12) United States Patent
Matsushita et al.

(10) Patent No.: US 10,308,908 B2
(45) Date of Patent: Jun. 4, 2019

(54) METHOD OF PRODUCING ETHANOL USING CONTINUOUS CULTURE AND CONTINUOUS CULTURE APPARATUS

(71) Applicant: TOYOTA JIDOSHA KABUSHIKI KAISHA, Toyota-shi, Aichi-ken (JP)

(72) Inventors: Hibiki Matsushita, Nagoya (JP); Emiko Tominaga, Chiryu (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 14/927,935

(22) Filed: Oct. 30, 2015

(65) Prior Publication Data
US 2016/0122785 A1 May 5, 2016

(30) Foreign Application Priority Data

Oct. 31, 2014 (JP) .................. 2014-223469

(51) Int. Cl.
| | |
|---|---|
| C12M 3/00 | (2006.01) |
| C12M 1/00 | (2006.01) |
| C12M 1/36 | (2006.01) |
| C12M 1/34 | (2006.01) |
| C12P 7/10 | (2006.01) |

(52) U.S. Cl.
CPC ............ C12M 41/48 (2013.01); C12M 21/12 (2013.01); C12M 41/32 (2013.01); C12P 7/10 (2013.01); *C12P 2203/00* (2013.01); *Y02E 50/16* (2013.01); *Y02E 50/17* (2013.01)

(58) Field of Classification Search
CPC ....... C12M 41/30; C12M 41/32; C12M 41/36
See application file for complete search history.

(56) References Cited

U.S. PATENT DOCUMENTS

2009/0048816 A1* 2/2009 Srinivasa ............... C12M 41/48
 703/11
2010/0285574 A1* 11/2010 Genta ................ B01D 11/0226
 435/289.1

(Continued)

FOREIGN PATENT DOCUMENTS

| EP | 2 143 802 A1 | 1/2010 |
|---|---|---|
| JP | 2005-514951 A | 5/2005 |

(Continued)

OTHER PUBLICATIONS

Eliasson A. et al., "Anaerobic Xylose Fermentation by Recombinant *Saccharomyces cerevisiae* Carrying XYL1, XYL2, and XKS1 in Mineral Medium Chemostat Cultures," Applied and Environmental Microbiology, vol. 8, No. 8, Aug. 2000, p. 3381-3386.

(Continued)

*Primary Examiner* — Nathan A Bowers
(74) *Attorney, Agent, or Firm* — Sughrue Mion, PLLC

(57) ABSTRACT

A method of producing ethanol includes: measuring a xylose concentration in a culture fluid that contains microorganisms having xylose utilizing ability, the culture fluid including a culture medium that contains saccharides derived from lignocellulose; and performing an addition control in which an additional culture medium is added to the culture fluid to conduct a continuous culture of the microorganisms, the additional culture medium containing saccharides derived from lignocellulose.

9 Claims, 4 Drawing Sheets

(56) References Cited

U.S. PATENT DOCUMENTS

| | | | |
|---|---|---|---|
| 2011/0081672 A1* | 4/2011 | Andersen | C12M 21/12 435/22 |
| 2013/0095538 A1 | 4/2013 | Katahira et al. | |
| 2015/0093829 A1* | 4/2015 | Swanda | C12M 23/22 435/420 |
| 2016/0002674 A1 | 1/2016 | Onishi et al. | |

FOREIGN PATENT DOCUMENTS

| | | |
|---|---|---|
| JP | 2009-065970 A | 4/2009 |
| JP | 2010-227074 A | 10/2010 |
| JP | 2011-147445 A | 8/2011 |
| JP | 2014-176351 A | 9/2014 |
| JP | 2014-193152 A | 10/2014 |
| WO | 03/062430 A1 | 7/2003 |
| WO | 2008/120644 A1 | 10/2008 |

OTHER PUBLICATIONS

Toivari MN et al., "Conversion of Xylose to Ethanol by Recombinant *Saccharomyces cerevisiae*: Importance of Xylulokinase (XKS1) and Oxygen Availability," Metabolic Engineering 3, 236-249 (2001).
Becker et al., "High-Efficiency Transformation of Yeast by Electroporation," Cloning and Recombinant DNA, Methods in Enzymology, vol. 194 (6 pages total).
Hinnen et al., "Transformation of Yeast," Proc. Natl. Acad. Sci. USA, vol. 75 No. 4, pp. 1929-1933, Apr. 1978.
Ito et al., "Transformation of Intact Yeast Cells Treated with Alkali Cations," Journal of Bacteriology, Jan. 1983, p. 163-168.
Attilio Converti et al. "A New Kinetic Approach to the Fermentation of Multisubstrate Complex Media", Applied Biochemistry and Biotechnology, 1991, vol. 30, pp. 361-373.
Lisbeth Olsson et al., "Fermentation of lignocellulosic hydrolysates for ethanol production", Enzyme and Microbial Technology, 1996, vol. 18, pp. 312-331.
Päivi Ylitervo et al., "Impact of Furfural on Rapid Ethanol Production Using a Membrane Bioreactor", Energies, 2013, vol. 6, pp. 1604-1617.
Kuang Zhang et al., "Removal of the Fermentation Inhibitor, Furfural, Using Activated Carbon in Cellulosic-Ethanol Production", Industrial and Engineering Chemistry Research, 2011, vol. 50, pp. 14055-14060.
Gengsheng, J., et al., "Continuous Fermentation of Pentose by Pichia Stipitis with Low-pH Treatment", Chinese Doctoral Dissertations Full-text Database (Engineering Science and Technology I), 2005, Issue 2, B018-4, 9 pages.
Partial Machine Translation of communication dated Jul. 4, 2018, from the State Intellectual Property Office of the P.R.C. in counterpart Chinese application No. 201510710881.0.

* cited by examiner

F I G . 4
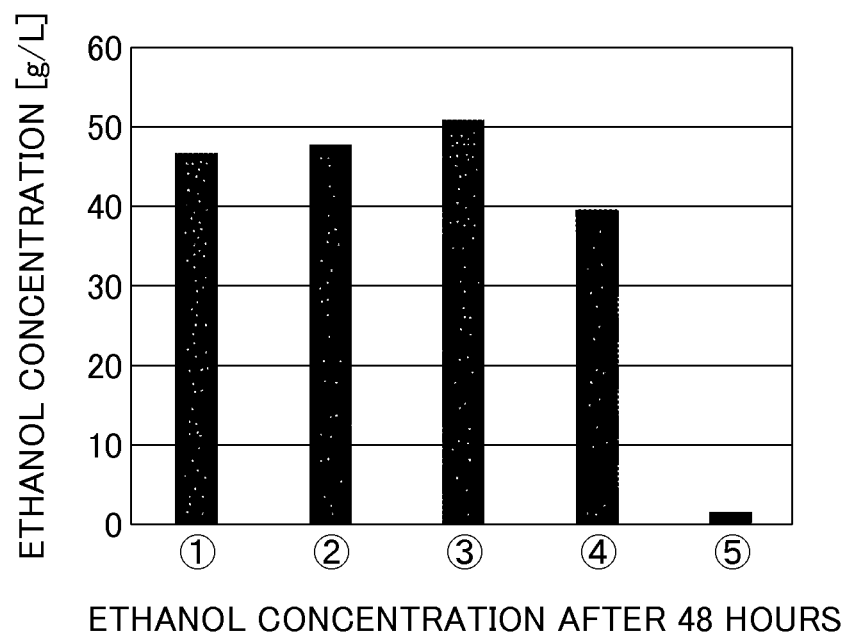
ETHANOL CONCENTRATION AFTER 48 HOURS

METHOD OF PRODUCING ETHANOL USING CONTINUOUS CULTURE AND CONTINUOUS CULTURE APPARATUS

INCORPORATION BY REFERENCE

The disclosure of Japanese Patent Application No. 2014-223469 filed on Oct. 31, 2014 including the specification, drawings and abstract is incorporated herein by reference in its entirety.

BACKGROUND OF THE INVENTION

1. Field of the Invention

The present invention relates to a method of producing ethanol using continuous culture in which recombinant microorganisms having xylose-metabolizing ability is used; and a continuous culture apparatus.

2. Description of Related Art

Main saccharides contained in lignocellulose include glucose constituting cellulose and xylose constituting hemicellulose. When lignocellulose is chemically or enzymatically decomposed, a saccharified composition containing monosaccharides such as glucose and xylose as major components is obtained. In order to industrially produce a useful material from lignocellulose, microorganisms which can be fermented with high yield and high productivity by efficiently using saccharides contained in the saccharified composition; and a production process are required.

For example, genes encoding xylose isomerase (XI), xylose reductase (XR), and xylitol dehydrogenase (XDH) are transferred to a yeast having high ethanol fermentation ability such as *Saccharomyces cerevisiae* to impart xylose utilizing ability to a yeast. With this yeast, ethanol can be produced by efficiently using saccharides derived from lignocellulose.

In general, as a method of producing by fermentation a material using microorganisms, batch culture, continuous culture, and feeding culture (fedbatch culture) are known. In batch culture, a new culture medium is prepared for each process, microorganisms are inoculated into the prepared culture medium, and another culture medium is not added until the end of the culture. In batch culture, the quality of each culture varies, but the risk of contamination can be dispersed and reduced. In continuous culture, a culture medium is supplied to a culture system at a constant rate, and concurrently, a culture fluid is extracted from the culture system at the same rate. Continuous culture is characterized in that a constant culture environment is easily maintained and productivity is stable. In feeding culture, a culture medium or a specific component of a culture medium is added to a culture system during the culture, and the obtained product is not extracted from the culture system until the end of the culture.

In particular, in regard to continuous culture, Japanese Patent Application Publication No. 2009-065970 (JP 2009-065970 A) discloses a method of producing a chemical product by continuous fermentation in which high productivity can be stably maintained over a long period of time under simple operating conditions. In the method disclosed in JP 2009-065970 A, a fermentation culture fluid is filtered through a porous film, and microorganisms and the like are extracted from the fermentation culture fluid to the outside of the system. However, in this method, when a lignocellulose-based material is used, the clogging of the porous film occurs, and there is a problem in that high cost is required to solve the clogging.

Japanese Patent Application Publication No. 2010-227074 (JP 2010-227074 A) discloses a method of continuously producing ethanol by alcohol fermentation in which a yeast is used with a starchy material as a substrate. In the method disclosed in JP 2010-227074 A, continuous fermentation conditions including fermentation temperature, substrate supply rate, fermentation liquid extraction rate, air flow rate, and yeast concentration are controlled to specific values, and the ethanol concentration in the fermentation liquid is maintained to be a predetermined value or lower. According to the method disclosed in JP 2010-227074 A, the production of ethanol can be efficiently continued without additional supply of a yeast during continuous fermentation. However, in the continuous culture method disclosed in JP 2010-227074 A, when saccharides derived from lignocellulose are used as a substrate, there is a problem in that ethanol cannot be efficiently produced.

SUMMARY OF THE INVENTION

As described above, in the related art, ethanol cannot be efficiently produced from saccharides derived from lignocellulose by using microorganisms having xylose utilizing ability. In consideration of the above-described circumstances, the invention provides a method and apparatus that achieves an efficient produce of ethanol from saccharides derived from lignocellulose by continuous culture in which microorganisms having xylose utilizing ability are used.

As a result of thorough research, the present inventors found that, in continuous culture in which microorganisms having xylose utilizing ability are used, ethanol can be efficiently produced by controlling the addition of culture medium with the xylose concentration in a culture fluid as an index, thereby completing the invention.

A method of producing ethanol according one aspect of the invention includes: measuring a xylose concentration in a culture fluid that contains microorganisms having xylose utilizing ability, the culture fluid including a culture medium that contains saccharides derived from lignocellulose; and performing an addition control in which an additional culture medium is added to the culture fluid to conduct a continuous culture of the microorganisms, the additional culture medium containing saccharides derived from lignocellulose. In the method of producing ethanol according to the above aspect of the invention, the addition control may include adding the additional culture medium to the culture fluid, to adjust the xylose concentration to be a preset threshold or lower. In the method of producing ethanol according to the above aspect of the invention, the preset threshold may be ⅓ or lower of a xylose concentration in the culture fluid before start of culture. In the method of producing ethanol according to the above aspect of the invention, the preset threshold may be 10 g/L or lower. In the method of producing ethanol according to the above aspect of the invention, the addition control may include controlling a supply rate of the additional culture medium to the culture fluid such that the number of cells of microorganisms used for ethanol production produced per unit time and unit liquid volume in the continuous culture is more than the number of cells of microorganisms used for ethanol production produced per unit time and unit liquid volume in a batch culture in which the culture medium is used. In the method of producing ethanol according to the above aspect of the invention, the supply rate is higher than F which may be obtained from the following equation $$F = V \times (x_{max} - x_0)/x_s \times T/(t_{batch} \times (T - t_i))$$

where F represents a supply rate of the additional culture medium, V represents a liquid volume of the culture fluid, $x_{max}$ represents a maximum concentration of microorganisms used for ethanol production in the batch culture in which the culture medium is used, $x_0$ represents a concentration of microorganisms used for ethanol production at a start of the batch culture in which the culture medium is used, $x_s$ represents a concentration microorganisms used for ethanol production in a steady state of the continuous culture in which the culture medium is used, T represents a time for which the steady state is maintained in the culture fluid, $t_{batch}$ represents a total time required for the batch culture in which the culture medium is used, and $t_i$ represents a total time required until the steady state is established in the continuous culture in which the culture medium is used. In the method of producing ethanol according to the above aspect of the invention, the supply rate may be controlled such that the xylose concentration in the culture fluid is 10 times or lower a xylose concentration in the culture fluid at an end of the batch culture in which the culture medium is used. In the method of producing ethanol according to the above aspect of the invention, the culture medium may contain a saccharified solution that is obtained by performing a saccharification treatment on lignocellulose after a steam treatment using a dilute acid. In the method of producing ethanol according to the above aspect of the invention, the culture medium may contain a saccharified solution that is obtained by performing a saccharification treatment on lignocellulose after a steam treatment without using a dilute acid and in which a concentration of excessively decomposed saccharides in the saccharified solution is 400 ppm to 1500 ppm. A continuous culture apparatus according to one aspect of the invention includes: a culture tank in which microorganisms having xylose utilizing ability are continuously cultured in a culture medium containing saccharides derived from lignocellulose; a culture medium supply section that is configured to perform a supply of an additional culture medium to the culture tank, the additional culture medium containing saccharides derived from lignocellulose; a xylose concentration measuring section that is configured to measure a xylose concentration in a culture fluid in the culture tank; and a controller that is configured to control the supply based on the xylose concentration. In the continuous culture apparatus according to the above aspect of the invention, the controller may be configured to control the supply such that the xylose concentration is adjusted to be a preset threshold or lower. In the continuous culture apparatus according to the above aspect of the invention, the preset threshold may be ⅓ or lower of a xylose concentration in the culture fluid before start of culture. In the continuous culture apparatus according to the above aspect of the invention, the preset threshold may be 10 g/L or lower. In the continuous culture apparatus according to the above aspect of the invention, the controller may be configured to control a supply rate of the additional culture medium to the culture fluid such that the number of cells of microorganisms used for ethanol production produced per unit time and unit liquid volume in the continuous culture is more than the number of cells of microorganisms used for ethanol production produced per unit time and unit liquid volume in a batch culture in which the culture medium is used. In the continuous culture apparatus according to the above aspect of the invention, the supply rate may be higher than F which is obtained from the following equation $$F = V \times (x_{max} - x_0)/x_s \times T/(t_{batch} \times (T - t_i))$$

where F represents a supply rate of the additional culture medium, V represents a liquid volume of the culture fluid, $x_{max}$ represents a maximum concentration of microorganisms used for ethanol production in the batch culture in which the culture medium is used, $x_0$ represents a concentration of microorganisms used for ethanol production at a start of the batch culture in which the culture medium is used, $x_s$ represents a concentration of microorganisms used for ethanol production in a steady state of the continuous culture in which the culture medium is used, T represents a time for which the steady state is maintained in the culture fluid, $t_{batch}$ represents a total time required for the batch culture in which the culture medium is used, and $t_i$ represents a total time required until the steady state is established in the continuous culture in which the culture medium is used. In the continuous culture apparatus according to the above aspect of the invention, the supply rate may be controlled such that the xylose concentration in the culture fluid is 10 times or lower a xylose concentration in the culture fluid at an end of the batch culture in which the culture medium is used. In the continuous culture apparatus according to the above aspect of the invention, the culture medium contains a saccharified solution that is obtained by performing a saccharification treatment on lignocellulose after a steam treatment using a dilute acid. In the continuous culture apparatus according to the above aspect of the invention, the culture medium may contain a saccharified solution that is obtained by performing a saccharification treatment on lignocellulose after a steam treatment without using a dilute acid and in which a concentration of excessively decomposed saccharides in the saccharified solution is 400 ppm to 1500 ppm.

In the method of producing ethanol and the continuous culture apparatus according to an aspect of the invention, the addition of the additional culture medium is controlled based on the xylose concentration in the culture fluid. Therefore, the production efficiency of ethanol using microorganisms having xylose utilizing ability can be significantly improved.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 4 is a characteristic diagram showing a relationship between a concentration of excessively decomposed saccharides and ethanol productivity.

DETAILED DESCRIPTION OF EMBODIMENTS

Hereinafter, one embodiment of the invention will be described more specifically with reference to the drawings and Examples. In a method of producing ethanol according to the embodiment of the invention, microorganisms having xylose utilizing ability are continuously cultured in a culture medium containing saccharides derived from lignocellulose, thereby producing ethanol. In particular, in the method of producing ethanol according to the embodiment of the invention, when an additional culture medium containing saccharides derived from lignocellulose is continuously added, addition control of the additional culture medium including adjustment of addition amount, adjustment of addition rate, and adjustment of addition timing is determined based on a xylose concentration in a culture fluid.

Figure 1:
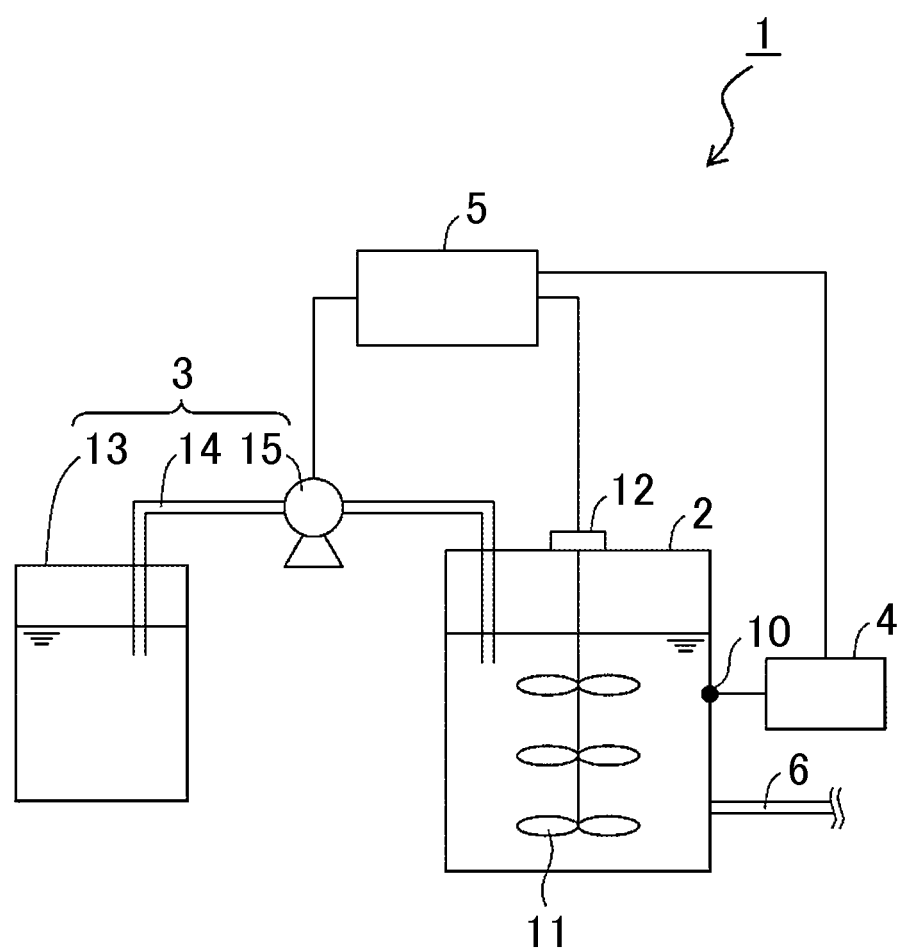
FIG. 1 is a schematic configuration diagram showing an example of a continuous culture apparatus to which one embodiment of the invention is applied.

The method of producing ethanol according to the embodiment of the invention can be realized using, for example, a continuous culture apparatus 1 shown in FIG. 1.

The continuous culture apparatus 1 includes: a culture tank 2 in which microorganisms having xylose utilizing ability are continuously cultured in a culture medium containing saccharides derived from lignocellulose; a culture medium supply section 3 that supplies an additional culture medium, which contains saccharides derived from lignocellulose, to the culture tank 2; a xylose concentration measuring section 4 that measures a xylose concentration in a culture fluid of the culture tank 2; and a controller 5 that controls the supply of the additional culture medium, which is performed by the culture medium supply section 3, based on the xylose concentration. The continuous culture apparatus 1 further includes a discharge section 6 that extracts the culture fluid at the same rate as that of the additional culture medium supplied from the culture medium supply section 3.

For example, the culture tank 2 includes a sampling portion 10 that aseptically extracts the culture fluid from the inside of the culture tank 2 and can be connected to the xylose concentration measuring section 4 through the sampling portion 10. Although not particularly limited thereto, the culture tank 2 includes: impellers 11; and a drive controller 12 that controls the driving of the impellers 11. At this time, the drive controller 12 can control the driving of the impellers 11 based on a control signal output from the controller 5. Although not shown, the culture tank 2 may further include: means for measuring the number of cells contained in the culture fluid; means for measuring the dissolved oxygen concentration or the dissolved carbon dioxide concentration in the culture fluid; means for measuring the concentrations of glucose, ethanol, and the like in the culture fluid; and means for measuring the concentration of excessively decomposed saccharides in the culture fluid.

For example, the culture medium supply section 3 includes: an additional culture medium tank 13 that is filled with the additional culture medium containing saccharides derived from lignocellulose; and a pump 15 that is provided in a culture medium flow path 14 through which the additional culture medium tank 13 and the culture tank 2 are connected. The culture medium supply section 3 controls the driving of the pump 15 based on a control signal output from the controller 5 and can adjust the addition timing, addition amount, and addition flow rate of the additional culture medium supplied from the additional culture medium tank 13 to the culture tank 2.

As described above, the xylose concentration measuring section 4 is connected to the culture tank 2, for example, through the sampling portion 10 and measures the xylose concentration in the culture fluid of the culture tank 2. A method of measuring the xylose concentration in the culture fluid is not particularly limited. For example, an enzymatic method can be used. In the enzymatic method, an enzyme reaction is caused to occur using an enzyme with xylose as a substrate, and the obtained product is quantitatively analyzed based on a change in absorbance. As a result, the xylose concentration can be measured. The xylose concentration may also be measured with a method using high-performance liquid chromatography.

Unlike the above-described configuration, the xylose concentration measuring section 4 may be provided as an individual device independent of the culture tank 2 without being connected to the culture tank 2 through the sampling portion 10. In this case, the operator may aseptically extract the culture fluid from the culture tank 2 such that the xylose concentration measuring section 4 can measure the xylose concentration in the extracted culture fluid.

The xylose concentration in the culture fluid measured by the xylose concentration measuring section 4 is input to the controller 5. The controller 5 outputs a control signal to the culture medium supply section 3 to control the addition of the additional culture medium based on the input xylose concentration. Specifically, the controller 5 compares the input xylose concentration in the culture fluid to a preset threshold and outputs a control signal to supply the additional culture medium to the culture tank 2 such that the xylose concentration in the culture fluid of the culture tank 2 is adjusted to be the threshold or lower. At this time, by controlling the flow rate and the addition timing of the additional culture medium based on the xylose concentration in the additional culture medium, the xylose concentration in the culture fluid of the culture tank 2 can be adjusted to be the threshold or lower.

The threshold is not particularly limited and may be a value at which xylose contained in the culture fluid is sufficiently consumed. For example, the threshold may be ⅓ or lower of the xylose concentration in the culture fluid, with which the culture tank 2 is filled, before start of culture. More specifically, the threshold may be 10 g/L or lower.

By adjusting the xylose concentration in the culture fluid to be the threshold or lower, ethanol fermentation using saccharides derived from lignocellulose, that is, using glucose and xylose can sufficiently progress. As a result, ethanol can be produced with high efficiency.

On the other hand, it is preferable that the controller 5 compares the input xylose concentration in the culture fluid to a preset value (hereinafter, referred to as "lower limit value") and outputs a control signal to supply the additional culture medium to the culture tank 2 such that the xylose concentration in the culture fluid of the culture tank 2 is adjusted to be the lower limit value or higher. The lower limit value described herein refers to the xylose concentration that is determined such that the productivity of ethanol production in the continuous culture using the continuous culture apparatus 1 is higher than the productivity of ethanol production in batch culture.

Specifically, it is preferable that the controller 5 controls the supply rate of the additional culture medium such that the number of cells of microorganisms used for ethanol production produced per unit time and unit liquid volume in the continuous culture using the continuous culture apparatus 1 is more than the number of cells of microorganisms used for ethanol production produced per unit time and unit liquid volume in batch culture using the same culture fluid as that in the continuous culture. More specifically, the supply rate of the additional culture medium can be set to be higher than F which is obtained from the following Equation (1).

$$F = V \times (x_{max} - x_0)/x_s \times T/(t_{batch} \times (T - t_i)) \quad (1)$$

In the equation, F represents the supply rate of the additional culture medium, V represents the liquid volume of the culture fluid, $x_{max}$ represents a maximum concentration of microorganisms used for ethanol production in the batch culture in which the culture medium is used, $x_0$ represents a concentration of microorganisms used for ethanol production at the start of the batch culture in which the culture medium is used, $x_s$ represents a concentration of microorganisms used for ethanol production in a steady state of the continuous culture in which the culture medium is used, T represents a time for which the steady state is maintained in the culture fluid, $t_{batch}$ represents a total time required for the batch culture in which the culture medium is used, and $t_i$ represents a total time required until a steady state is established in the continuous culture in which the culture medium is used.

This equation is based on the following facts: that the number of cells of microorganisms used for ethanol production $R_{batch}$ produced per unit time and unit liquid volume in the batch culture is obtained from the following equation; and that the number of cells of microorganisms used for ethanol production $R_{cont}$ produced per unit time and unit liquid volume in the continuous culture in which the continuous culture apparatus 1 is used is obtained from the following equation. That is, the Equation (1) is obtained by arranging the details of F assuming that $R_{batch}=R_{cont}$.

$$R_{batch}=(x_{max}-x_0)/t_{batch}$$

$$R_{cont}=D \times x_s \times (1-t_i/T)$$

In the equation, D represents a dilution ratio, and D=F/V

As another example of the lower limit value, the controller 5 may set the lower limit value based on the xylose concentration at the end of the batch culture in which the same culture medium is used. That is, by setting the lower limit value to be higher than the xylose concentration (for example, to be higher than 10 times) at the end of the batch culture in which the same culture medium is used, the productivity of ethanol production using the continuous batch can exceed that of ethanol production using the batch culture.

As described above, when ethanol is produced from a culture medium containing saccharides derived from lignocellulose by continuous culture, addition control of an additional culture medium including adjustment of addition amount, adjustment of addition rate, and adjustment of addition timing is determined based on a xylose concentration in a culture fluid. As a result, superior ethanol production efficiency can be achieved.

That is, saccharides derived from lignocellulose, such as glucose and xylose, contained in the culture fluid can be used with high efficiency for ethanol fermentation. In general, in a fermentation production process of a material using continuous culture, the addition control of an additional culture medium is performed while monitoring the concentration of microorganisms used for ethanol production in a culture fluid. However, in ethanol production in which a culture medium containing saccharides derived from lignocellulose is used, an increase-decrease profile in concentration of microorganisms used for ethanol production is not linked with a profile of ethanol concentration in a culture fluid, and the response of the increase-decrease profile in concentration of microorganisms used for ethanol production to the profile of ethanol concentration in a culture fluid is delayed. Therefore, the concentration of microorganisms used for ethanol production is poor in sensitivity as an index indicating the process degree of ethanol fermentation. In addition, a profile of the concentration of glucose among saccharides derived from lignocellulose does not have a relationship with a profile of ethanol concentration in a culture fluid and thus is not suitable as an index indicating the process degree of ethanol fermentation. Further, in order to use the exhaust gas concentration from a culture fluid as the index, it is necessary to provide a measuring device for measuring carbon dioxide, which causes an increase in the cost of the apparatus. Moreover, since ventilation is not actively performed in ethanol fermentation, it is not efficient to measure the exhaust gas concentration. When the ethanol concentration in a culture fluid is used as the index, the process degree of ethanol fermentation can be directly monitored because ethanol is a production target. However, since the production amount of ethanol is half of that of xylose, a variation in ethanol concentration is also half of that in the xylose concentration. Accordingly, as compared to a case where the xylose concentration is measured, the ethanol concentration is not sufficient in sensitivity as an index indicating the process degree of ethanol fermentation.

As described above, when ethanol is produced from the culture medium containing saccharides derived from lignocellulose by the continuous culture, far superior ethanol production efficiency can be achieved by performing the addition control of the additional culture medium based on the xylose concentration in the culture fluid.

Ethanol produced as described above can be collected from the culture fluid, which is discharged from the discharge section 6, using a conventional method. A method of collecting ethanol is not particularly limited, and any well-known method of the related art can be used. For example, after the above-described ethanol fermentation is finished, a liquid layer containing ethanol and a solid layer containing recombinant microorganisms and solid components are separated from each other by solid-liquid separation. Next, ethanol is separated from the liquid layer and purified using an distillation method. As a result, ethanol having a high purity can be collected. The purification degree of ethanol can be appropriately adjusted according to the intended use of ethanol.

Figure 2:
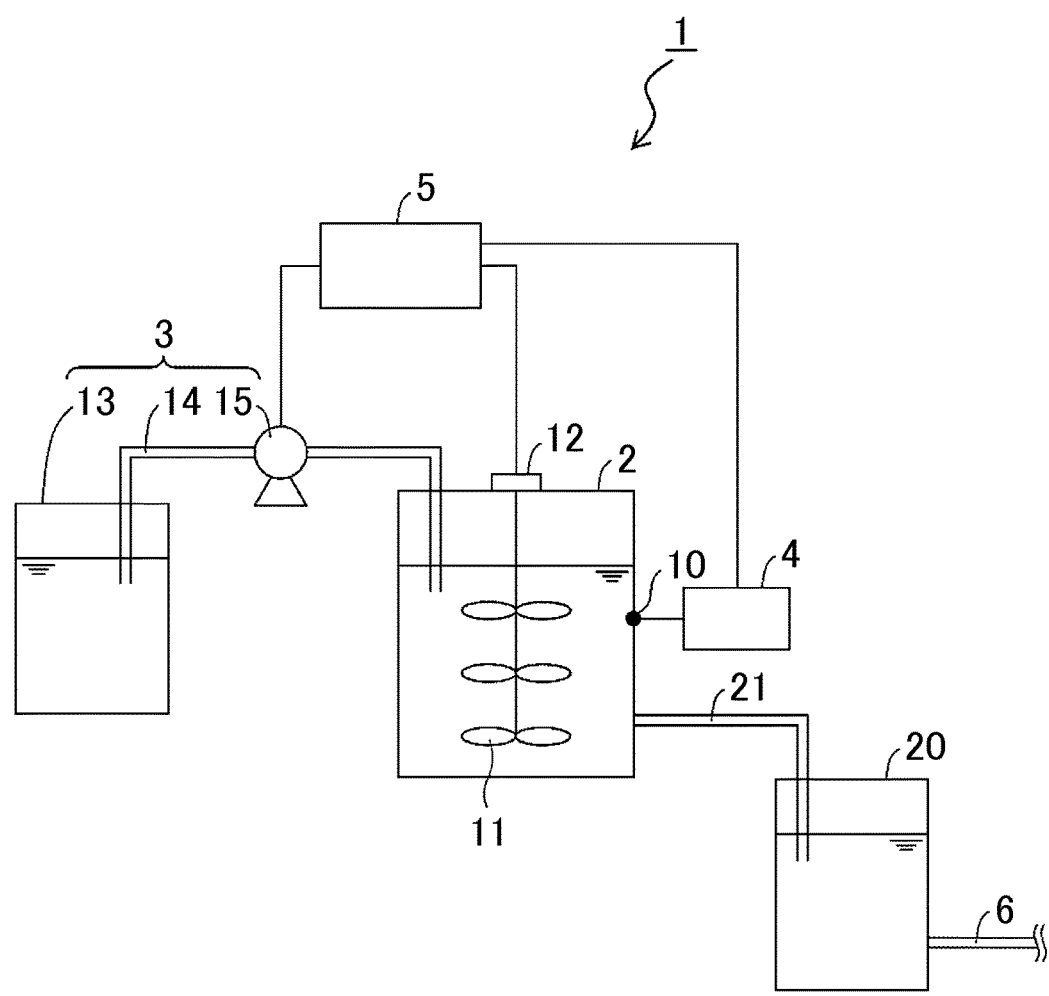
FIG. 2 is a schematic configuration diagram showing another example of a continuous culture apparatus to which the embodiment of the invention is applied.

The continuous culture apparatus 1 to which the embodiment of the invention is applied is not limited to the configuration shown in FIG. 1 and, as shown in FIG. 2, may have a configuration including: the culture tank 2; and a second-stage culture tank 20 that is connected to the culture tank 2. That is, in the continuous culture apparatus 1 shown in FIG. 2, the culture tank 2 and the second-stage culture tank 20 are connected to each other through a pipe 21, and the discharge section 6 that extracts the culture fluid after the end of the ethanol fermentation is provided in the second-stage culture tank 20. In the continuous culture apparatus 1 shown in FIG. 2, as in the case of the continuous culture apparatus 1 shown in FIG. 1, the xylose concentrations in the culture tank 2 and the second-stage culture tank 20 are measured, respectively, such that the addition control of the additional culture medium can be performed based on the xylose concentrations.

Hereinafter, the microorganisms having xylose utilizing ability will be described. The meaning of the microorganisms having xylose utilizing ability includes not only microorganisms inherently having xylose-metabolizing ability but also recombinant microorganisms obtained by transferring a xylose metabolism-related gene to microorganisms inherently having xylose-metabolizing ability or microorganism not having xylose-metabolizing ability. Here, the meaning of the xylose metabolism-related gene includes a xylose isomerase gene, a xylose reductase gene encoding xylose reductase that converts xylose into xylitol, a xylitol dehydrogenase gene encoding xylitol dehydrogenase that converts xylitol into xylulose, and a xylulokinase gene encoding xylulokinase that phosphorylates xylulose to produce xylulose 5-phosphate. Xylulose 5-phosphate produced from xylulokinase is metabolized through the pentose phosphate pathway.

More specifically, the xylose isomerase gene (XI gene) among the xylose metabolism-related genes is not particularly limited, any gene derived from a species may be used. For example, plural xylose isomerase genes derived from intestinal protists of termite disclosed in Japanese Patent Application Publication No. 2011-147445 (JP 2011-147445 A) can be used without any particular limitation. In addition, as the xylose isomerase gene, a gene derived from *Piromyces* sp. E2 which is an anaerobic fungus (refer to Published Japanese Translation of PCT application No. 2005-514951 (JP-A-2005-514951)), a gene derived from *Cyllamyces aberensis* which is an anaerobic fungus, a gene derived from *Bacteroides thetaiotaomicron* which is a bacterium, a gene derived from *Clostridium phytofermentans* which is a bacterium, or a gene derived from *Streptomyces murinus* cluster can be used. Specifically, as the xylose isomerase gene, a xylose isomerase gene derived from an intestinal protist of *Reticulitermes Speratus* can be preferably used.

The xylose metabolism-related gene is not particularly limited, and examples thereof include a xylose reductase gene and a xylitol dehydrogenase gene derived from *Pichia stipitis* and a xylulokinase gene derived from *Saccharomyces cerevisiae* (refer to Eliasson A. et al., Appl. Environ. Microbiol, 66: 3381-3386 and Toivari M N et al., Metab. Eng. 3: 236-249). As the xylose reductase gene, a xylose reductase gene derived from *Candida tropicalis* or *Candida parapsilosis* can be used. As the xylitol dehydrogenase gene, a xylitol dehydrogenase gene derived from *Candida tropicalis* or *Candida parapsilosis* can be used. As the xylulokinase gene, a xylulokinase gene derived from *Pichia stipitis* can be used.

Microorganisms which can be used as a host are not particularly limited, and examples thereof include molds such as *Aspergillus*, yeasts, and microorganisms such as bacteria. In particular, a yeast having alcohol fermentation ability or a bacterium having alcohol fermentation ability can be used. More specific examples of *Aspergillus* include *Aspergillus aculeatus* and *Aspergillus oryzae*. As the yeast, various well-known yeasts of the related art can be used, and examples thereof include a *Saccharomyces* yeast such as *Saccharomyces cerevisiae*, a *Schizosaccharomyces* yeast such as *Schizosaccharomyces pombe*, a *Candida* yeast such as *Candida shehatae*, a *Pichia* yeast such as *Pichia stipitis*, a *Hansenula* yeast, a *Klocckera* yeast, a *Schwanniomyces* yeast, a *Yarrowia* yeast, a *Trichosporon* yeast, a *Brettanomyces* yeast, a *Pachysolen* yeast, a *Yamadazyma* yeast, a *Kluyveromyces* yeast such as *Kluyveromyces marxianus* or *Kluveromyces lactis*, and an *Issatchenkia* yeast such as *Issatchenkia orientalis*. From the viewpoint of industrial use, a *Saccharomyces* yeast is preferable. In particular, *Saccharomyces cerevisiae* is preferable. Examples of the bacterium having alcohol fermentation ability include a *Zymomonas* bacterium such as *Zymomonas mobilis*.

In particular, a promoter of the xylose metabolism-related gene to be transferred is not particularly limited. For example, a promoter of a glyceraldehyde-3-phosphate dehydrogenase (TDH3) gene, a promoter of a 3-phosphoglycerate kinase (PGK1) gene, or a promoter of a hyperosmolarity-responsive 7 (HOR7) gene can be used. Among these, a promoter of Pyruvate decarboxylase (PDC1) gene is preferable because it is capable of high expression of a target gene on a downstream side.

That is, the above-described gene may be transferred to the genome of a yeast together with an expression-regulation promoter and other expression-regulatory regions. Alternatively, the above-described gene may be transferred to the genome of a yeast which is a host such that the expression thereof is regulated by a gene of an inherent gene and other expression-regulatory regions.

As a method of transferring the above-described gene, any method which is well-known as a microorganism transformation method can be used. Specific examples of the method include the electroporation method "Meth. Enzym., 194, p. 182, (1990)", the spheroplast technique "Proc. Natl. Acad. Sci., U.S.A., 75, p. 1929, (1978)", and the lithium acetate method "J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual". However, the method is not limited to these examples.

Hereinafter, the culture medium containing saccharides derived from lignocellulose will be described. The culture medium containing saccharides derived from lignocellulose refers to a composition which contains a saccharified solution containing saccharides, the saccharified solution being obtained by performing a saccharification treatment on cellulosic biomass containing lignocellulose. When the saccharification treatment is performed on the cellulosic biomass, a well-known pretreatment of the related art may be performed. The pretreatment is not particularly limited, and examples thereof include a treatment of decomposing lignin using microorganisms and a crushing treatment of cellulosic biomass. As the pretreatment, for example, a treatment of dipping crushed cellulosic biomass in a dilute sulfuric acid solution, an alkali solution, an ionic liquid, a hydrothermal treatment, a pulverizing treatment, or a steam explosion treatment using a dilute acid can be adopted. Due to these pretreatments, the saccharification rate of biomass can be improved.

The cellulosic biomass which is the target of the saccharification treatment refers to biomass containing a complex of the crystal structure of cellulose fiber, hemicellulose, and lignin. In particular, the crystal structure of cellulose fiber and hemicellulose are treated as polysaccharides contained in a cellulosic biomass. Examples of the cellulosic biomass include waste materials such as timber from forest thinning, construction waste, industrial waste, household waste, agricultural waste, waste timber, forest residues, and waste paper. Further, examples of the cellulosic biomass include corrugated cardboard, waste paper, old newspapers, magazines, pulp, and pulp sludge. Furthermore, examples of the cellulosic biomass include pellets obtained by crushing, compressing, and molding waste timber such as sawdust or wood shavings, forest residues, waste paper, and the like.

The cellulosic biomass may be used in any form. In particular, in the case of so-called soft biomass, it is preferable that a compression treatment is performed thereon, and in the case of so-called hard biomass, it is preferable that a crushing treatment is performed thereon. The compression treatment of soft biomass refers to a treatment of applying a predetermined pressure to soft biomass so as to relax and disrupt biomass tissue. For the compression treatment, a compressor which is typically used in the fields of food and agriculture can be used. The crushing treatment of hard biomass refers to a treatment of crushing biomass using, for example, a device such as a cutter mill. In the crushing treatment, it is preferable that hard biomass is crushed into a size of, for example, 0.1 mm to 2 mm as average particle size.

The saccharification treatment refers to a treatment of causing cellulase and/or microorganisms capable of secretory production of cellulase to act on the above-described cellulosic biomass. Due to the saccharification treatment, cellulose and hemicellulose contained in the cellulosic biomass are saccharified into monosaccharides (soluble saccharides) such as glucose, mannose, galactose, xylose, and arabinose.

In particular, it is preferable that the above-obtained culture medium containing saccharides derived from lignocellulose contains a saccharified solution which is obtained by performing a saccharification treatment on lignocellulose after a steam treatment using a dilute acid (one of the pretreatments). Alternatively, it is preferable that the above-obtained culture medium containing saccharides derived from lignocellulose contains a saccharified solution which is obtained by performing a saccharification treatment on lignocellulose without performing a steam treatment and in which the concentration of excessively decomposed saccharides in the saccharified solution is 400 ppm to 1500 ppm. The excessively decomposed saccharides refer to 5-HMF and furfural. That is, when the steam treatment without using a dilute acid is performed, it is preferable to use a saccharified solution which is performed by performing a saccharification treatment on lignocellulose and in which the total concentration of 5-HMF, furfural, and the like is 400 ppm to 1500 ppm. Even when the steam treatment using a dilute acid is not performed, the concentration of excessively decomposed saccharides may be within the above-described range.

When the saccharified solution, which is obtained by performing the saccharification treatment on lignocellulose after the stem treatment (one of the pretreatments) using a dilute acid, is used as the culture medium, the propagation of unwanted microorganisms can be suppressed in the above-described ethanol fermentation for a long period of time, and ethanol can be produced by the continuous culture for a long period of time.

Even when the steam treatment using a dilute acid is not performed, the propagation of unwanted microorganisms can be suppressed in the ethanol fermentation for a long period of time by using a saccharified solution containing 400 ppm or higher of excessively decomposed saccharides as the culture medium. When the concentration of excessively decomposed saccharides is 1500 ppm or lower, the production amount of ethanol in the ethanol fermentation can be maintained to be high.

Hereinafter, one embodiment of the invention will be described in more detail using Examples, but the technical scope of the invention is not limited to the following Examples.

Hereinafter, Example 1 of the invention will be described. In this example, continuous culture was performed using a xylose-utilizing yeast (*Saccharomyces cerevisiae*), and a relationship between the addition rate of an additional culture medium (a saccharified solution containing saccharides derived from lignocellulose) and concentrations including ethanol concentration, glucose concentration, and xylose concentration was examined.

In the continuous fermentation, the continuous culture apparatus 1 shown in FIG. 1 was used. This apparatus includes a 1 L culture tank, a pump, and a tube through which the components are connected. A discharge port was provided in the middle of the culture tank used in this example. Therefore, when the liquid level rises, a fermentation liquid was discharged. The addition rate of the additional culture medium (saccharified solution) is controlled by the flow rate of the pump.

Hereinafter, the continuous fermentation of Example 1 will be described. First, the preparation of the saccharified solution used in the continuous fermentation will be described. Using dilute sulfuric acid, a steam explosion pretreatment was performed to obtain a culture medium containing napier grass. The culture medium consists of napier grass-treated product: 15% (w/w (in terms of dry mass)), cellulase: 1.2% (w/w), and water: 83.8%. In the steam explosion pretreatment, sulfuric acid was added such that the dry weight of napier grass was 2 wt %, the water content in napier grass was adjusted to 70%, a steam treatment was performed at 190° C. for 9 minutes, and a explosion treatment (a physical crushing method in which, under high-temperature and high-pressure conditions, the pressure was instantly released to be the atmospheric pressure) was performed. A Rocking mixer (RM-10-3, manufactured by Aichi Electric Co., Ltd.) was charged with 4980 g of the culture medium containing napier grass to perform a saccharification reaction. Saccharification conditions were 50° C., 72 hours, and the rotating speed of 80 rpm. Next, the obtained reaction liquid was collected as a saccharified solution used in the following continuous fermentation.

Next, the continuous fermentation will be described. 22.7 g of a culture fluid containing a xylose-utilizing yeast, which was grown in a YPD culture medium, was inoculated into a 1 L fermenter in which 477.3 g of the above-prepared culture medium containing saccharides derived from napier grass. Next, fermentation (32° C., 250 rpm, pH 5.5) was started. After 48 days from the start of the fermentation, the continuous addition of the above-prepared saccharified solution was started. Concurrently, the discharge of the fermentation liquid was started by opening the discharge port. Here, the addition rate of the saccharified solution was set to 97 g/h (48 h to 383 h), 181 g/h (383 h to 623 h), or 139 g/h (623 h to 815 h).

Figure 3:
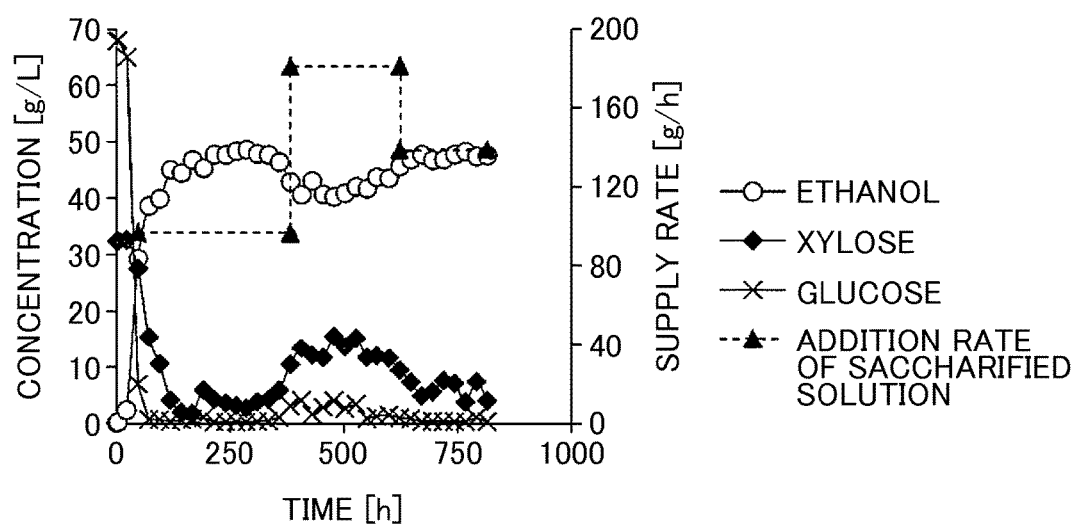
FIG. 3 is a characteristic diagram showing a relationship between an addition rate of a culture medium (saccharified solution) containing saccharides derived from lignocellulose and concentrations including an ethanol concentration, a xylose concentration, and a glucose concentration.

By appropriately performing sampling during the fermentation, the ethanol concentration, the glucose concentration, and the xylose concentration were measured. Each of the concentrations was measured by high-performance liquid chromatography (LC-10A (manufactured by Shimadzu Corporation), detector: RI, column: Aminex HPX-87H, temperature: 30° C., mobile phase: 0.01 N, flow rate: 0.6 mL/min). The results are shown in FIG. 3. In this continuous fermentation, the contamination of unwanted microorganisms was not observed, and the continuous fermentation was able to be continued for about one month.

As shown in FIG. 3, during the continuous fermentation period, the ethanol concentration, the glucose concentration, and the xylose concentration were dependent on the supply rate of the saccharified solution, and the following results were obtained: when the supply rate was increased, the ethanol concentration decreased, and the xylose concentration increased (the glucose concentration slightly increased); and when the supply rate was decreased, the ethanol concentration increased, and the xylose concentration decreased (the glucose concentration slightly decreased).

The above results show: that the process degree of ethanol fermentation can be monitored based on the xylose concentration in the culture medium; and that the productivity of ethanol can be improved by performing the addition control of the additional culture medium based on the monitored process degree. In particular, in this example, it was verified that a state where the ethanol concentration is high can be maintained by supplying the additional culture medium at a rate at which the xylose concentration in the culture fluid is 10 g/L or lower.

Hereinafter, experiments to verify a relationship between a method of adjusting the culture fluid containing saccharides derived from lignocellulose and the contamination of unwanted microorganisms and a relationship between the concentration of excessively decomposed saccharides in the culture fluid and the contamination of unwanted microorganisms will be described.

First, a steam treatment was performed on napier grass under various conditions (Table 1), and napier grass was suspended at a ratio of 6% in terms of dry mass. In Table 1, the treatment time of 0 min represents a treatment of decreasing the temperature immediately after the temperature reached a preset value.

TABLE 1

| Steam Treatment Conditions | | | | | | |
|---|---|---|---|---|---|---|
| | (1) | (2) | (3) | (4) | (5) | (6) |
| Temperature | 180° C. | 190° C. | 200° C. | 200° C. | 200° C. | 190° C. |
| Time | 0 min | 0 min | 0 min | 5 min | 5 min | 9 min |
| Treatment Using Dilute Acid | Not Performed | Not Performed | Not Performed | Not Performed | Not Performed | Performed |
| Water content | 90% | 90% | 90% | 90% | 90% | 70% |

* The treatment time of 0 min represents a treatment of decreasing the temperature immediately after the temperature reached a preset value.

Next, cellulase was added, and a saccharification treatment (pH 6, 55° C., 75 hr, 900 rpm) was performed in a 1 L container. The obtained saccharified solution was put into a 50 mL centrifuge tube, and the centrifuge tube was left to stand at room temperature without being covered with a lid. Next, whether or not the contamination of unwanted microorganisms occurred was determined by visual inspection.

The results are shown in Table. 2. Symbols in Table 2 represent the following meanings.

−: unwanted microorganisms were not confirmed by visual inspection
+: unwanted microorganisms were slightly confirmed by visual inspection
++: Half of the liquid surface was covered with unwanted microorganisms
+++: The entire region of the liquid surface was covered with unwanted microorganisms

TABLE 2

| Results of Unwanted microorganisms Contamination | | | | | | |
|---|---|---|---|---|---|---|
| | Unwanted Microorganisms Contamination State | | | | | |
| | (1) | (2) | (3) | (4) | (5) | (6) |
| 4 Days | + | + | − | − | − | − |
| 1 Week | ++ | ++ | + | − | − | − |
| 2 Weeks | +++ | +++ | +++ | + | − | − |
| 3 Weeks | +++ | +++ | +++ | +++ | + | − |
| 1 Month | +++ | +++ | +++ | +++ | +++ | + |
| 2 Months | +++ | +++ | +++ | +++ | +++ | + |

As shown in Table 2, four days were required under Conditions (1) and (2), one week was required under Condition (3), and two weeks or longer was required under Conditions (4), (5), and (6) until unwanted microorganisms were confirmed by visual inspection. Under Condition (6), a small amount of unwanted microorganisms were observed after one month; however, the growth of unwanted microorganisms did not progress any more. The above results show that: when the culture fluid, which is obtained by performing the saccharification treatment on lignocellulose after the steam treatment using a dilute acid, is used, the propagation of unwanted microorganisms can be suppressed in the above-described ethanol fermentation for a long period of time, and ethanol can be produced by the continuous culture for a long period of time.

The concentration of excessively decomposed saccharides at the end of the saccharification treatment is as shown in Table 3. The unit of the numerical values in Table 3 is ppm.

TABLE 3

| Concentration of Excessively Decomposed Saccharides (Unit: ppm) | | | | | | |
|---|---|---|---|---|---|---|
| | (1) | (2) | (3) | (4) | (5) | (6) |
| Furfural | 44 | 151 | 235 | 406 | 599 | 186 |
| 5HMF | 2 | 5 | 9 | 17 | 151 | 25 |
| Total | 46 | 156 | 244 | 423 | 750 | 211 |

The results of Table 3 show that: even when the steam treatment without using a dilute acid is performed, the propagation of unwanted microorganisms can be suppressed in the ethanol fermentation for a long period of time by using a culture fluid containing 400 ppm or higher of excessively decomposed saccharides.

An effect of an increase in the concentration of excessively decomposed saccharides on ethanol production was verified. First, 1 mL of a culture fluid containing a xylose-utilizing yeast, which was grown in a YPD culture medium, was inoculated into each of 500 mL Erlenmeyer flasks (1) to (5) in which 100 g of a culture medium having a composition shown in Table 4 was stored. Next, a fermentation test (32° C., 80 rpm) was started. By performing sampling after 48 hours from the start of the fermentation, the ethanol concentration was measured. The ethanol concentration was measured by high-performance liquid chromatography (LC-10A (manufactured by Shimadzu Corporation), detector: RI, column: Aminex HPX-87H, temperature: 30° C., mobile phase: 0.01 N sulfuric acid, flow rate: 0.6 mL/min).

| | (1) | (2) | (3) | (4) | (5) |
|---|---|---|---|---|---|
| Glucose | 8% | 8% | 8% | 8% | 8% |
| Xylose | 4% | 4% | 4% | 4% | 4% |
| Yeast Extract | 1% | 1% | 1% | 1% | 1% |
| Polypeptone | 2% | 2% | 2% | 2% | 2% |
| Furfural | 0 ppm | 500 ppm | 1000 ppm | 1500 ppm | 2000 ppm |
| 5HMF | 0 ppm | 100 ppm | 200 ppm | 300 ppm | 400 ppm |

The results of measuring the ethanol concentration after 48 hours from the start of the fermentation are shown in FIG. 4. As can be seen from FIG. 4, in the Erlenmeyer flask (3) in which the concentration of excessively decomposed saccharides (furfural, 5HMF) as fermentation inhibitors was 1200 ppm, there were no effects on the ethanol fermentation. In the Erlenmeyer flasks (4) and (5) in which the concentration of excessively decomposed saccharides exceeded 1800 ppm, the productivity of ethanol was decreased.

The above results clarify that: even when the steam treatment without using a dilute acid is performed, the contamination of unwanted microorganisms can be prevented and high ethanol productivity can be maintained for a long period of time by adjusting the concentration of excessively decomposed saccharides to be 400 ppm to 1500 ppm.

What is claimed is:

1. A continuous culture apparatus comprising:
    a culture tank in which microorganisms having xylose utilizing ability are continuously cultured in a culture medium containing saccharides derived from lignocellulose;
    a culture medium supply section that is programmed to perform a supply of an additional culture medium to the culture tank, the additional culture medium containing saccharides derived from lignocellulose, and wherein the additional culture medium does not contain the microorganisms;
    a xylose concentration measuring section that is programmed to measure a xylose concentration in a culture fluid in the culture tank; and
    a controller that is programmed to control the supply based on the measured xylose concentration, such that the xylose concentration is adjusted to be a preset threshold or lower, wherein said preset threshold is ⅓ or lower of the xylose concentration in the culture fluid before the start of culturing, wherein the controller is programmed to control a supply rate of the additional culture medium to the culture fluid such that the number of cells of microorganisms used for ethanol production produced per unit time and unit liquid volume in the continuous culture is more than the number of cells of microorganisms used for ethanol production produced per unit time and unit liquid volume in a batch culture in which the culture medium is used,
    and wherein the supply rate is higher than F which is obtained from the following equation $$F = V \times (x_{max} - x_0) / x_s \times T / (t_{batch} \times (T - t_i))$$

where F represents a supply rate of the additional culture medium,
    V represents a liquid volume of the culture fluid,
    $x_{max}$ represents a maximum concentration of microorganisms used for ethanol production in the batch culture in which the culture medium is used,
    $x_0$ represents a concentration of microorganisms used for ethanol predilection at a start of the batch culture in which the culture medium is used,
    $x_s$ represents a concentration of microorganisms used for ethanol production in a steady state of the continuous culture in which the culture medium is used,
    T represents a time for which the steady state is maintained in the culture fluid,
    $t_{batch}$ represents a total time required for the batch culture in which the culture medium is used, and
    $t_i$ represents a total time required until the steady state is established in the continuous culture in which the culture medium is used.

2. The continuous culture apparatus according to claim 1, wherein
    the supply rate is controlled such that the xylose concentration in the culture fluid is 1 times or lower a xylose concentration in the culture fluid at an end of the batch culture in which the culture medium is used.

3. The continuous culture apparatus according to claim 1, wherein
    the culture medium contains a saccharified solution that is obtained by performing a saccharification treatment on lignocellulose after a steam treatment using a dilute acid.

4. The continuous culture apparatus according to claim 1, wherein
    the culture medium contains a saccharified solution that is obtained by performing a saccharification treatment on lignocellulose without performing a steam treatment using a dilute acid and in which a concentration of excessively decomposed saccharides in the saccharified solution is 400 ppm to 1500 ppm.

5. The continuous culture apparatus according to claim 1, wherein the xylose concentration is adjusted to be the preset threshold or lower by controlling the supply of an additional culture medium containing saccharides when the measured concentration is greater than the preset threshold.

6. A continuous culture apparatus comprising:
    a culture tank in which microorganisms having xylose utilizing ability are continuously cultured in a culture medium containing saccharides derived from lignocellulose;
    a culture medium supply section that is programmed to perform a supply of an additional culture medium to the culture tank, the additional culture medium containing saccharides derived from lignocellulose, and wherein the additional culture medium does not contain the microorganisms;
    a xylose concentration measuring section that is programmed to measure a xylose concentration in a culture fluid in the culture tank; and
    a controller that is programmed to control the supply based on the measured xylose concentration, such that the xylose concentration is adjusted to be a preset threshold or lower, wherein said preset threshold is 10 g/L or lower.

7. The continuous culture apparatus according to claim 6, wherein the xylose concentration is adjusted to be the preset threshold or lower by controlling the supply of an additional culture medium containing saccharides when the measured concentration is greater than the preset threshold.

8. A continuous culture apparatus comprising:
    a culture tank in which microorganisms having xylose utilizing ability are continuously cultured in a culture medium containing saccharides derived from lignocellulose;
    a culture medium supply section that is programmed to perform a supply of an additional culture medium to the culture tank, the additional culture medium containing saccharides derived from lignocellulose, and wherein the additional culture medium does not contain the microorganisms;
    a xylose concentration measuring section that is programmed to measure a xylose concentration in a culture fluid in the culture tank; and
    a controller that is programmed to control the supply based on the measured xylose concentration, wherein the controller is programmed to control a supply rate of the additional culture medium to the culture fluid such that the number of cells of microorganisms used for ethanol production produced per unit time and unit liquid volume in the continuous culture is more than the number of cells of microorganisms used for ethanol production produced per unit time and unit liquid volume in a batch culture in which the culture medium is used, and wherein the supply rate is higher than F which is obtained from the following equation $$F = V \times (x_{max} - x_0)/x_s \times T/(t_{batch} \times (T - t_i))$$

where F represents a supply rate of the additional culture medium,

V represents a liquid volume of the culture fluid, $x_{max}$ represents a maximum concentration of microorganisms used for ethanol production in the batch culture in which the culture medium is used, $x_0$ represents a concentration of microorganisms used for ethanol production at a start of the batch culture in which the culture medium is used, $x_s$ represents a concentration of microorganisms used for ethanol production in a steady state of the continuous culture in which the culture medium is used, T represents a time for which the steady state is maintained in the culture fluid, $t_{batch}$ represents a total time required for the batch culture in which the culture medium is used, and $t_i$ represents a total time required until the steady state is established in the continuous culture in which the culture medium is used.

9. The continuous culture apparatus according to claim 8, wherein the xylose concentration is adjusted to be a preset threshold or lower by controlling the supply of an additional culture medium containing saccharides when the measured concentration is greater than the preset threshold.

* * * * *